United States Patent
Stenberg

(10) Patent No.: US 7,525,093 B2
(45) Date of Patent: Apr. 28, 2009

(54) LIQUID OR GAS SENSOR AND METHOD

(75) Inventor: Johan Stenberg, Delsbo (SE)

(73) Assignee: Medair AB, Delsbo (SE)

( * ) Notice: Subject to any disclaimer, the term of this patent is extended or adjusted under 35 U.S.C. 154(b) by 183 days.

(21) Appl. No.: 10/583,208

(22) PCT Filed: Dec. 19, 2003

(86) PCT No.: PCT/SE03/02041

§ 371 (c)(1),
(2), (4) Date: Jun. 16, 2006

(87) PCT Pub. No.: WO2005/059524

PCT Pub. Date: Jun. 30, 2005

(65) Prior Publication Data

US 2007/0101800 A1   May 10, 2007

(51) Int. Cl.
*G01J 5/02* (2006.01)
(52) U.S. Cl. ..................................... 250/343
(58) Field of Classification Search ................. 250/343
See application file for complete search history.

(56) References Cited

U.S. PATENT DOCUMENTS

| | | | |
|---|---|---|---|
| 5,060,508 A * | 10/1991 | Wong | 73/31.02 |
| 5,282,473 A | 2/1994 | Braig et al. | |
| 5,834,777 A * | 11/1998 | Wong | 250/343 |
| 5,932,877 A | 8/1999 | Braig et al. | |
| 6,444,474 B1 * | 9/2002 | Thomas et al. | 436/146 |
| 6,600,558 B2 * | 7/2003 | Ueno et al. | 356/246 |
| 2005/0017206 A1 * | 1/2005 | Tice et al. | 250/573 |

OTHER PUBLICATIONS

Patent abstracts of Japan, vol. 200, No. 303, May 5, 2003 & JP 20-02328086 Nov. 15, 2002.
Patent abstracts of Japan, vol. 200, No. 305, May 12, 2003 & JP 20-03017537 Jan. 17, 2003.

* cited by examiner

*Primary Examiner*—David P Porta
*Assistant Examiner*—Marcus H Taningco
(74) *Attorney, Agent, or Firm*—Dilworth & Barrese LLP

(57) ABSTRACT

A fluid sensor is provided which contains a fluid cell (1) to enclose a volume of fluid (7), i.e., a gas or liquid, to be analyzed, in addition to a method for producing such a fluid sensor. An electromagnetic energy source (3) is arranged to transmit electromagnetic waves (4) into the fluid cell (1) with at least one detector (5) arranged to detect electromagnetic waves passing through the fluid cell (1) and at least one opening (2) situated for inlet or outlet of the fluid (7) to be analyzed. A circuit board (8, 10, 11, 12, 13, 14, 15, 16) is arranged to evaluate intensity of electromagnetic waves reaching the detector (5) and/or provide circuitry for the electromagnetic energy source (3). At least part of the fluid cell (1) is incorporated into the substrate of the circuit board (8, 10, 11, 12, 13, 14, 15, 16).

23 Claims, 2 Drawing Sheets

LIQUID OR GAS SENSOR AND METHOD

BACKGROUND OF THE INVENTION

TECHNICAL FIELD OF THE INVENTION AND PRIOR ART

The present invention concerns a fluid sensor, i.e. a sensor for a gas or a liquid, such as a non-dispersive infrared (NDIR)-type sensor, containing a fluid cell to enclose a volume of gas or liquid that is to be analysed. The fluid sensor comprises an electromagnetic energy source arranged to transmit electromagnetic waves into the fluid cell and at least one detector to detect electromagnetic waves passing through the fluid cell and at least one opening for the inlet/outlet of gas that is to be analysed. The gas sensor also comprises a circuit board to evaluate the intensity of electromagnetic waves reaching said at least one detector and/or to provide the circuitry for the electromagnetic energy source. The present invention also relates to a method for producing such a fluid sensor.

Gas sensors of the NDIR-type are well known in the art. Such sensors comprise a gas cell with an IR-source at one end and an IR-detector at the other. A gas containing molecules of the gas that is to be analysed diffuse into the gas cell and IR-light is directed through the gas cell towards the detector. The detector has a filter in front of it which eliminates all light except the specific wavelength that the gas that is to be analysed absorbs. Since the other gas molecules in the gas cell do not absorb light at that specific wavelength, only the molecules of the gas that is to be analysed affect the amount of light reaching the detector. The intensity of the light of the specific wavelength that reaches the detector is therefore inversely proportional to the concentration of the gas to be detected in the gas cell. The higher the concentration of such a gas, the more light of this wavelength will be attenuated.

The gas cell of a gas sensor usually comprises a metal body that is polished so as to reflect the light passing through the gas cell. Alternatively the gas cell may be made of moulded or extruded plastic components that are glued together and sputtered with a material that is reflective to the electromagnetic waves passing through the gas cell. The process of producing a gas cell is therefore a relatively complex and expensive task and requires special tools to produce the gas cell.

Furthermore, when such gas sensors are used condensation collects on the inner walls of the gas cell which deteriorates the quality of the signals passing through the gas cell and this can adversely affect the analysis results.

SUMMARY OF THE INVENTION

The object of the present invention is to provide an accurate and compact fluid sensor that is simple and inexpensive to construct.

This object is fulfilled using a fluid sensor, i.e. a gas sensor or a liquid sensor, containing a fluid cell to enclose a volume of liquid or gas that is to be analysed where the fluid cell has an electromagnetic energy source arranged to transmit electromagnetic waves into the fluid cell and at least one detector to detect electromagnetic waves passing through the fluid cell and at least one opening for the inlet/outlet of fluid, i.e. liquid or gas, that is to be analysed. The fluid sensor comprises a circuit board to evaluate the intensity of electromagnetic waves reaching said at least one detector and/or to provide the circuitry for the electromagnetic energy source. An array of detectors is used if several gases are to be analyzed at the same time.

At least part of the fluid cell is incorporated into the substrate of the circuit board i.e. the dielectric material on which the circuit is printed, etched or formed. By "at least part of the fluid cell" it is meant at least part of an internal wall along which electromagnetic waves will be transmitted.

According to a preferred embodiment of the invention at least part of the internal walls of the fluid cell are coated with a material that is reflective to the electromagnetic waves passing through the fluid cell so as to reduce the attenuation of the electromagnetic signal being transmitted through the fluid cell at the cell walls. This means that the attenuation of the signal will be, as far as possible, due only to its absorption by molecules of the fluid being analysed. According to a preferred embodiment of the invention the reflective material is a metal such as gold or silver.

A fluid sensor always requires a circuit board to evaluate the intensity of electromagnetic waves reaching said at least one detector and/or to provide the circuitry for the electromagnetic energy source and so a circuit board is a component that always has to be manufactured for a fluid sensor. A circuit board is also usually gold plated since gold is a good conductor and does not corrode.

The circuit board may contain via-holes extending through the whole or part of the circuit board to conduct current from one part, or side, of the circuit board to another. These via holes are holes going through the whole, or part, of the circuit board substrate and are also usually gold plated and so are ideal for use as a fluid cell. This means that it is relatively simple to construct a fluid cell in the substrate of a circuit board and that the time required to manufacture a fluid sensor can therefore be significantly reduced as no special tools to manufacture the fluid cell are required and the cost of producing a fluid sensor is consequently significantly reduced. The inventive fluid sensor is more portable than a conventional fluid sensor as it is more lightweight and compact than conventional fluid sensors which have a separate fluid cell, usually made of metal. The inventive fluid sensor may therefore be carried more easily.

Furthermore the condensation problem is decreased or eliminated since the electric/electronic components mounted on the circuit board generate heat which is conducted through the substrate of the circuit board. As the walls of the fluid cell are consequently heated this prevents condensation from collecting on the inner walls of the of the fluid cell. According to a preferred embodiment of the invention the circuit board of the fluid sensor comprises a heat-generating component in the vicinity of the fluid cell.

According to other preferred embodiments of the invention the fluid cell extends through the circuit board and/or across the circuit board, the fluid cell is either fully or partially embedded in the substrate of the circuit board depending on the size of the fluid cell and the thickness of the circuit board substrate. Part of the fluid cell may, for example, extend along a surface of the circuit board. The fluid cell may be completed using a metallized capping part mounted on the surface of the circuit board.

According to another preferred embodiment of the invention the electromagnetic energy source and/or said at least one detector is/are mounted on the circuit board so that the circuit board provides the foundation for the whole fluid sensor however the electromagnetic energy source and said at least one detector may be provided as separate components in communication with the fluid cell that is incorporated into the circuit board. However mounting both of these components on the circuit board is advantageous in that interconnecting wires or cables connecting the components to the circuit board are not needed and this eliminates the noise introduced by such interconnects, decreases the production time and makes the fluid sensor more compact.

According to a further preferred embodiment of the invention the electromagnetic energy source is a light source, such as an infrared light source and said at least one detector is an optical detector.

According to a preferred embodiment of the invention the fluid cell is built up of a plurality of circuit boards stacked together. One circuit board may for example contain one part of the fluid cell and one or more circuit boards may be placed on, under or beside the first circuit board so as to provide the complementary part or parts of the fluid cell.

According to another preferred embodiment of the invention the fluid sensor comprises a plurality of fluid cells incorporated into the substrate of the circuit board. Having a plurality of gas cells is advantageous if different sample gases are to be analyzed by the fluid sensor simultaneously. The fluid cells may be arranged so that a fluid may move freely between the fluid cells or from one cell to the next in a specific order. According to another preferred embodiment of the invention the plurality of fluid cells comprises at least one test channel to determine the attenuation at a wavelength not influenced by a fluid that is to be analysed, but close to it, to provide a measure of the variation of the electromagnetic signal influenced by environmental parameters and not by the analysed fluid.

According to a further preferred embodiment of the invention the fluid sensor comprises a flexible circuit board that may be bent into any desired shape.

The present invention also concerns a method for producing a fluid sensor having a fluid cell. The method comprises the step of forming a trench having at least one substantially smooth surface in the substrate of a circuit board along the path of the intended fluid cell, which will constitute at least part of a fluid cell. The expression "substantially smooth" is intended to mean a surface that is smooth enough to substantially avoid the introduction of distorted or spurious signals. Such a trench may be formed by selectively removing or displacing the substrate material with any technique known to those skilled in the art such as by laser, by etching or drilling.

According to a preferred embodiment of the invention the method comprises the further step of coating at least part of the, or each, wall of the trench with a material that is reflective to the electromagnetic waves that pass through the fluid cell, such as a metal. This material may be applied by an electrolytic, sputtering or any other suitable technique.

According to another preferred embodiment of the invention the method comprises the further step of stacking a plurality of circuit boards together so as to form a fluid cell.

The inventive fluid sensor is suitable for use in many applications including determining the concentration of a gas such as carbon dioxide, carbon monoxide, hydrocarbons, nitrous oxide or a liquid such as a liquid hydrocarbon or any other gas or liquid having attenuation bands in the infrared range. The fluid sensor is suitable for use in medical equipment such as a breathing monitor for determining the concentration of carbon dioxide in the exhaled air of a person or a person's breathing frequency or as a trace liquid or gas meter in ventilation and alarm systems for example. The inventive fluid sensor is also suitable for use to determine other properties of one or more fluids in the fluid cell such as pressure, structure or composition.

Further advantages as well as advantageous features of the invention appear from the following description.

The following description and drawings are not intended to limit the present invention to the embodiment disclosed The embodiments disclosed merely exemplify the principles of the present invention. The components shown in the figures are not drawn to scale.

DETAILED DESCRIPTION OF A PREFERRED EMBODIMENT OF THE INVENTION

Figure 1:
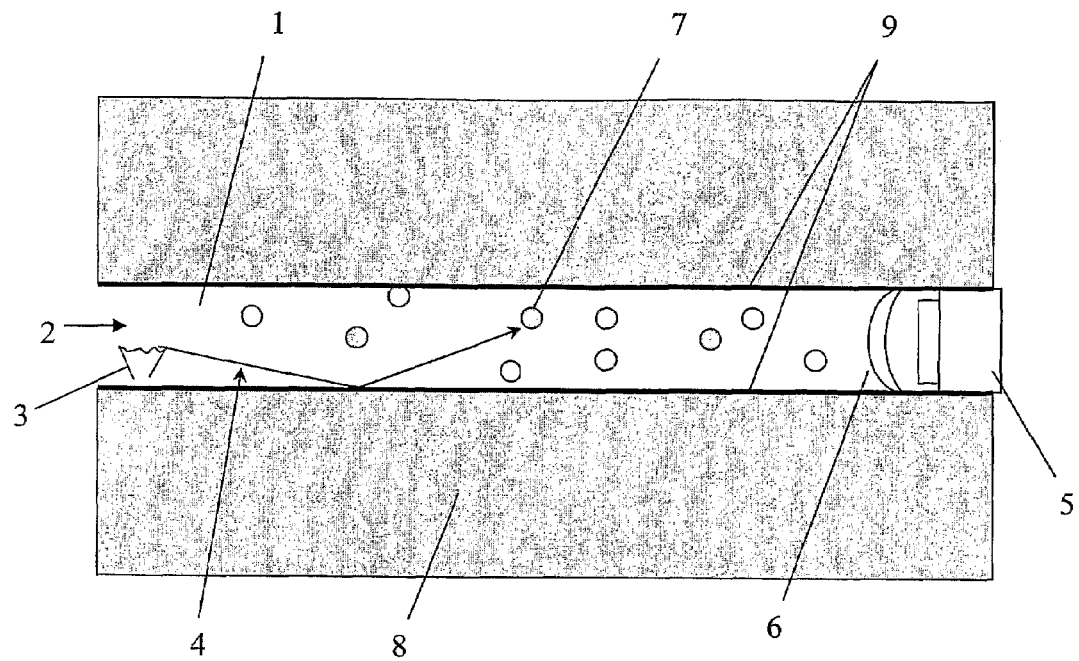
FIG. 1 is a schematic diagram of a gas sensor according to a preferred embodiment of the invention.

FIG. 1 shows carbon dioxide sensor containing a gas cell 1 to enclose a volume of gas, such as exhaled air from a person. The gas cell comprises an opening 2 for the inlet/outlet of gas that is to be analysed. The gas sensor comprises an IR-source 3, such as a heated element, arranged to transmit IR-radiation 4 into the gas cell and an IR-detector 5 to detect IR-radiation passing through the gas cell. The gas cell therefore functions as a waveguide for the IR-radiation.

A filter 6 is placed in front of the detector to eliminate all light except the specific wavelength that carbon dioxide molecules 7 absorb, namely 4.26 µm, which is in the IR-range. The intensity of 4.26 µm light that reaches the detector 5 is inversely proportional to the concentration of carbon dioxide in the sample of gas in the gas cell. When the concentration of carbon dioxide in the chamber is zero, the detector will detect the full light intensity from the IR-source. The exact relationship between IR-intensity and carbon dioxide concentration is determined by calibrating the gas sensor with pure nitrogen and a known concentration of carbon dioxide such as 5 vol % for example.

The gas cell 1 is incorporated into the substrate of a circuit board 8. The substrate comprises a ceramic material, a polymer, a composite or any other suitable dielectric material, and electric/electronic components are mechanically supported and electrically connected on the circuit board. A circuit board may also comprise multiple dielectric layers sandwiched between metal layers that are patterned to transfer signals between the electronic components.

The gas cell 1 is for example formed in the via-hole of the circuit board. The circuit board is used evaluate the intensity of IR-radiation reaching the detector 5 and to provide the circuitry for the IR-source 3. The inner walls of the gas cell are coated with a material 9 that is reflective to the IR-radiation passing through the gas cell 1, which allows the IR-signal to be totally reflected from one side of the gas cell to the other towards the IR-detector and consequently results in lower transmission losses.

Such a gas sensor may also be used to determine the structure or composition of a sample of gas in the gas cell.

Figure 2:
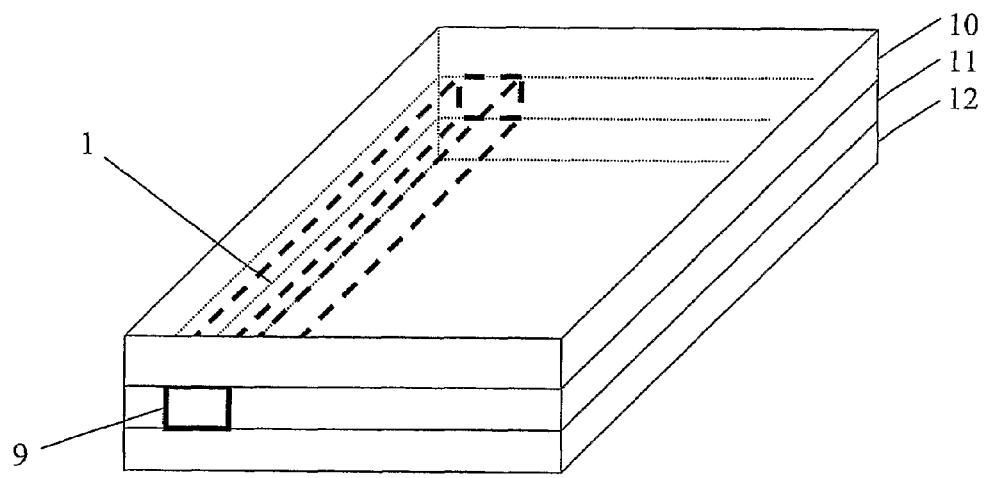
FIG. 2 shows part of a fluid sensor according to another preferred embodiment of the invention.

FIG. 2 shows a fluid cell 1 made up of three circuit boards 10, 11, 12, mounted on top one another. Circuit board 11, which comprises electric/electronic components has a gold-plated groove extending along the length of the circuit board which provides the side walls of the fluid cell 1. Circuit boards 10 and 12 provide the top and bottom walls of the fluid cell 1. Circuit boards 10 and 12 could however be replaced with gold- or silver-plated components placed above and below the groove in circuit board 11 to provide the top and bottom walls of the fluid cell 1.

The cross section of the fluid cell is rectangular in the example shown, it can however have any geometrical form such as circular, elliptical or square depending on the manufacturing process. The width of the fluid cell may be chosen by the user by varying the depth of the grooves. The optimal cross-sectional dimension of the fluid cell depends on the frequency of the electromagnetic waves being transmitted through the fluid cell and the desired transmission mode. Fluid cells having improper dimensions may distort the signal transmitted therethrough.

Although the fluid cell 1 extends through the circuit board 11 in a straight line, the invention is not limited to such fluid cells. The fluid cell 1 can have any geometrical form, it can be U-shaped for example. Having a non-straight fluid cell geometry means that a longer light absorption path can be created.

Figure 3:
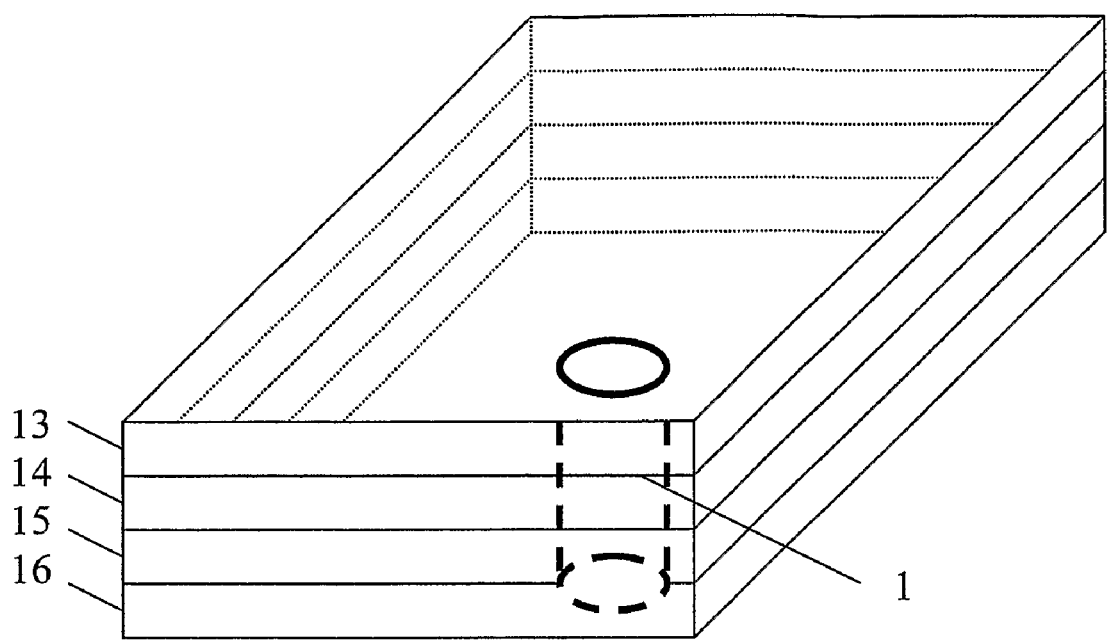
FIG. 3 shows part of a fluid sensor according to a further preferred embodiment of the invention.

FIG. 3 shows a fluid cell 1 with an elliptical cross-section formed by stacking four circuit boards 13, 14, 15, 16 on top of one another for example by overlapping their via-holes. The length of the fluid cell may therefore be varied by the user by choosing the amount of circuit boards that are to be stacked in this way. The fact that the fluid cell is easy to take apart also makes it easier to clean. Another advantage is that such stackability allows a multiparameter fluid sensor, for the analysis of several gases or which incorporates several sensors, to be easily constructed. The user can easily adapt the gas sensor to his/her specific needs by choosing or varying the length of the fluid cell.

The invention is of course not in any way restricted to the preferred embodiments thereof described above, but many possibilities to modifications thereof would be apparent to a man with ordinary skill in the art without departing from the basic idea of the invention as defined in the appended claims.

The invention claimed is:

1. Fluid sensor containing a fluid cell (1) to enclose a volume of fluid (7), i.e. gas or liquid to be analyzed, said fluid sensor comprising
    an electromagnetic energy source (3) arranged to transmit electromagnetic waves (4) into the fluid cell (1),
    at least one detector (5) to detect electromagnetic waves passing through the fluid cell (1) and situated directly downstream of said energy source (3) without any curves in said fluid cell (1),
    at least one opening (2) for the inlet/outlet of fluid to be analyzed, and
    a circuit board (8, 10, 11, 12, 13, 14, 15, 16) to evaluate the intensity of electromagnetic waves reaching said at least one detector (5) and/or to provide the circuitry for the electromagnetic energy source (3),
    at least part of the straight fluid cell (1) being incorporated into the substrate of the circuit board (8, 10, 11, 12, 13, 14, 15, 16).

2. Fluid sensor according to claim 1, which is a gas sensor.

3. Fluid sensor according to claim 1, wherein at least part of the internal walls of the fluid cell (1) are coated with a material (9) that is reflective to the electromagnetic waves (4) passing through the fluid cell (1).

4. Fluid sensor according to claim 3, wherein at least part of the internal walls of the fluid cell (1) are coated with a metal such as gold or silver.

5. Fluid sensor according to claim 1, wherein the electromagnetic energy source (3) and/or said at least one detector (5) is/are mounted on the circuit board (8, 10, 11, 12, 13, 14, 15, 16).

6. Fluid sensor according to claim 1, wherein the electromagnetic energy source (3) is a light source, such as an infrared light source and said at least one detector (5) is an optical detector.

7. Fluid sensor according to claim 1, wherein the circuit board of the fluid sensor comprises a heat-generating component in the vicinity of the fluid cell.

8. Fluid sensor according to claim 1, wherein the fluid cell extends through the circuit board (8, 10, 11, 12, 13, 14, 15, 16) and/or across the circuit board.

9. Fluid sensor according to claim 1, wherein the fluid cell (1) is fully embedded in the substrate of the circuit board (8, 10, 11, 12, 13, 14, 15, 16).

10. Fluid sensor according to claim 1, wherein the fluid cell (1) extends along a surface of the circuit board (8, 10, 11, 12, 13, 14, 15, 16).

11. Fluid sensor according to claim 1, comprising a plurality of fluid cells (1) incorporated into the substrate of the circuit board (8, 10, 11, 12, 13, 14, 15, 16).

12. Fluid sensor according to claim 11, wherein the plurality of fluid cells (1) comprises at least one test channel to determine the attenuation at a wavelength not influenced by a fluid (7) to be analyzed, but close to the fluid (7),
    to provide a measure of the variation of the electromagnetic signal influenced by environmental parameters and not by the analyzed fluid.

13. Fluid sensor according to claim 1, comprising a flexible circuit board (8, 10, 11, 12, 13, 14, 15, 16).

14. A fluid sensor according to claim 1, structured and arranged for determining the concentration of a gas (7) such as carbon dioxide, carbon monoxide, a hydrocarbon, nitrous oxide or a liquid hydrocarbon or any other gas or liquid having attenuation bands in the infrared range.

15. A fluid sensor according to claim 1, structured and arranged for determining the concentration of carbon dioxide in the exhaled air of a person or a person's breathing frequency.

16. A fluid sensor according to claim 1 which is a trace gas or liquid meter.

17. A fluid sensor according to claim 1, structured and arranged for determining the pressure, structure or composition of a gas or liquid.

18. A fluid sensor according to claim 1, wherein said fluid cell (1) extends entirely across the circuit board (8, 10, 11, 12, 13, 14, 15, 16) with said at least one opening (2) adjacent an edge of the circuit board (8, 10, 11, 12, 13, 14, 15, 16) and said detector (5) situated in an opening through an opposite edge of the circuit board (8, 10, 11, 12, 13, 14, 15, 16).

19. Fluid sensor containing a fluid cell (1) to enclose a volume of fluid (7), i.e. gas or liquid to be analyzed, said fluid sensor comprising
    an electromagnetic energy source (3) arranged to transmit electromagnetic waves (4) into the fluid cell (1),
    at least one detector (5) to detect electromagnetic waves passing through the fluid cell (1),
    at least one opening (2) for the inlet/outlet of fluid to be analyzed, and
    a circuit board (8, 10, 11, 12, 13, 14, 15, 16) to evaluate the intensity of electromagnetic waves reaching said at least one detector (5) and/or to provide the circuitry for the electromagnetic energy source (3),
    at least part of the fluid cell (1) being incorporated into the substrate of the circuit board (8, 10, 11, 12, 13, 14, 15, 16), and which is a liquid sensor.

20. Fluid sensor containing a fluid cell (1) to enclose a volume of fluid (7), i.e. gas or liquid to be analyzed, said fluid sensor comprising
    an electromagnetic energy source (3) arranged to transmit electromagnetic waves (4) into the fluid cell (1),
    at least one detector (5) to detect electromagnetic waves passing through the fluid cell (1), at least one opening (2) for the inlet/outlet of fluid to be analyzed, and a circuit board (8, 10, 11, 12, 13, 14, 15, 16) to evaluate the intensity of electromagnetic waves reaching said at least one detector (5) and/or to provide the circuitry for the electromagnetic energy source (3), at least part of the fluid cell (1) being incorporated into the substrate of the circuit board (8, 10, 11, 12, 13, 14, 15, 16), wherein the fluid cell (1) is built up of a plurality of circuit boards (8, 10, 11, 12, 13, 14, 15, 16) stacked together.

21. Method for producing a fluid sensor having a fluid cell (1), comprising the step of:

forming a straight trench having at least one substantially smooth surface in the substrate of a circuit board (8, 10, 11, 12, 12, 14, 15, 16) which will constitute at least part of a fluid cell;

and positioning at least one detector (5) to detect electromagnetic waves (4) passing through the fluid cell (1) and situated directly downstream of an energy source (3) in said straight trench.

22. Method according to claim 21, comprising the further step of coating at least part of the, or each, wall of the trench with a material (9) that is reflective to the electromagnetic waves (4) that pass through the fluid cell (1), such as metal.

23. Method for producing a fluid sensor having a fluid cell (1), comprising the step of forming a trench having at least one substantially smooth surface in the substrate of a circuit board (8, 10, 11, 12, 13, 14, 15, 16) which will constitute at least part of a fluid cell (1), and comprising the further step of stacking a plurality of circuit boards (8, 10, 11, 12, 13, 14, 15, 16) together to form a fluid cell (1).

\* \* \* \* \*